United States Patent [19]
Lattrell et al.

[11] Patent Number: 5,747,484
[45] Date of Patent: May 5, 1998

[54] CRYSTALLINE CEPHAM ACID ADDITION SALTS AND PROCESSES FOR THEIR PREPARATION

[75] Inventors: Rudolf Lattrell, Königstein; Walter Dürckheimer, Hattersheim; Peter Schmid, Stuttgart, all of Germany

[73] Assignee: Hoechst Aktiengesellschaft, Frankfurt am Main, Germany

[21] Appl. No.: 551,480

[22] Filed: Nov. 1, 1995

[30] Foreign Application Priority Data

Nov. 10, 1994 [DE] Germany .................. 44 40 141.8

[51] Int. Cl.$^6$ .................. A61K 31/545; C07D 501/46
[52] U.S. Cl. ............................. 514/202; 540/222
[58] Field of Search ...................... 540/222; 514/202

[56] References Cited

U.S. PATENT DOCUMENTS

| | | | |
|---|---|---|---|
| 4,609,653 | 9/1986 | Dürckheimer et al. | 540/222 |
| 4,845,087 | 7/1989 | Lattrell et al. | 514/202 |

FOREIGN PATENT DOCUMENTS

| | | |
|---|---|---|
| 0112550 | 7/1984 | European Pat. Off. |
| 0125576 | 11/1984 | European Pat. Off. |
| 0064740 | 4/1986 | European Pat. Off. |
| 3248281 | 6/1984 | Germany . |
| 3706020 | 9/1988 | Germany . |

OTHER PUBLICATIONS

R. Lattrell et al., The J. of Antibiotics vol. XLI No. 10: 1374–1394(1988).

*Primary Examiner*—Mukund J. Shah
*Assistant Examiner*—P. K. Sripada
*Attorney, Agent, or Firm*—Finnegan, Henderson, Farabow, Garrett & Dunner, L.L.P.

[57] ABSTRACT

Novel crystalline cephem acid addition salts and processes for their preparation
Compounds of the formula I

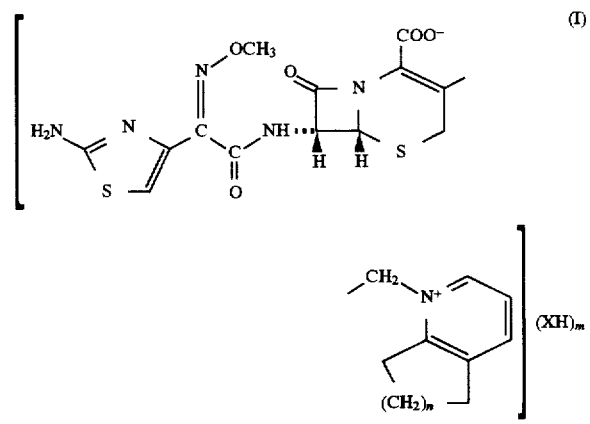

in which n is equal to 1 or 2 and m is 0.4–2.6, and where X is the anion of a carboxylic acid, have antibacterial activity.

9 Claims, 1 Drawing Sheet

Fig. 1

CRYSTALLINE CEPHAM ACID ADDITION SALTS AND PROCESSES FOR THEIR PREPARATION

The invention relates to novel crystalline cephem acid addition salts which are distinguished by particularly low solubility, processes for their preparation and their use as pharmaceuticals.

German Patent Applications DE 3 248 281 (U.S. Pat. No. 4,609,653) (for n=1) and DE 3 706 020 (U.S. Pat. No. 4,845,087) (for n=2) propose crystallized acid addition salts of the formula A which are used for the treatment of bacterial infections. Their active compound levels in the plasma, however, are not adequately long, in particular for use in the veterinary sector.

It is therefore an object of this invention to find salts having a half-life which is distinctly prolonged in comparison with the known salts and thus longer active compound levels in the plasma and tissues. This object is surprisingly achieved by salts of the formula I in which
n is equal to 1 or 2 and
m is 0.4–2.6, and where
X is the anion of a phenolic carboxylic acid of the formulae II a–d or the anion of a hydroxyphenylacetic acid of the formula III or the anion of a hydroxycinnamic acid of the formula IV or the anion of a hydroxyhippuric acid of the formula V where R and R' independently of one another are hydrogen, carboxyl, hydroxyl, halogen, a straight-chain or branched saturated or unsaturated aliphatic $C_1$–$C_5$-alkyl radical or $C_1$–$C_5$-alkoxy radical and where X can also be X/2 in the case of a diprotic acid.

Preferred compounds of the formula I contain the carboxylic acids of the formulae II–V, in which R and R' are hydrogen, carboxyl, hydroxyl, methyl or methoxy and in which m is 0.5–2.

The following acids, for example, are particularly preferred: dihydroxybenzoic acids, such as 2,4-, 2,5- or 3,5-dihydroxybenzoic acid, trihydroxybenzoic acids, such as gallic acid, hydroxydicarboxylic acids, such as 4-hydroxyisophthalic acid, hydroxynaphthalenecarboxylic acids, such as 2-hydroxy-naphthalene-1-carboxylic acid or 6-hydroxynaphthalene-1-carboxylic acid, methylenebishydroxybenzoic acids, such as 5,5'-methylene-bis-4-hydroxybenzoic acid, methylenebishydroxynaphthoic acids, such as embonic acid, hydroxycinnamic acids such as ferulic acid, hydroxyhippuric acids such as salicyluric acid.

A compound according to the invention where m=1 will be represented by way of example in simplified form by means of the following formula I'

The representation is a simplification because the actual structure in the salt and especially an exact localization of the charge are undetermined. The compounds where m is about 1 are particularly preferred.

The term XH in the abovementioned formula I can of course also include the anion of a diprotic acid, from which it follows that the term strictly speaking would then have to be $X_{1/2}H$.

The invention furthermore includes processes for the preparation of the salts of the formula I, which comprise 1. reacting a water-soluble salt of the formula I, for example a dihydrochloride, dihydroiodide or a sulfate, with salts of the carboxylic acids of the formula II, III, IV or V, or
2. reacting a cephem betaine of the formula VI in which n has the meaning mentioned for formula I, with the carboxylic acids of the formula II, III, IV or V.

The preparation of the water-soluble salts of the formula I is described in the patent applications cited above, and that of the betaine of the formula VI in European Patent EP 64740 (U.S. Pat. No. 5,071,979).

According to process 1, a water-soluble salt of the carboxylic acid II, III, IV or V, for example a sodium, potassium or magnesium salt, is added to a solution of one of these salts I in water, the underlying anion forming a poorly water-soluble acid addition salt of the formula I. These salts can be added in solid form or in aqueous solution or in mixtures of water and water-miscible organic solvents, e.g. methanol, ethanol, isopropanol, acetone, tetrahydrofuran and DMSO.

The formation of the salts of the formula I is carried out at temperatures between −10° and +60 C., preferably between +5° and +30° C. The crystallization of the salts takes place spontaneously during the addition of the salts of the carboxylic acids II–V, which are used in equimolar amounts up to an about 2.6-fold excess.

The process can also be carried out by initially introducing the salts of the carboxylic acids II–V and adding the acid addition salt I dissolved in water.

The salts of the formula I according to the invention are isolated by filtration or centrifugation and dried in a customary manner, for example by freeze-drying or with the aid of a dehydrating agent, e.g. potassium hydroxide or phosphorus pentoxide. Admixtures, e.g. of excess carboxylic acids II–V, can optionally be removed by stirring with a water-miscible organic solvent, such as acetone, ethanol or isopropanol.

Of course, by appropriate choice of the starting components poorly soluble salts can be obtained which contain a stoichiometric excess or deficit of the carboxylic acid, e.g. 0.4 mol to 2.6 mol of acid per mole of betaine of the formula VI. For example, the acid content in the salt of Example 1 can be reduced by treating with organic solvents, e.g. acetone or ethanol.

According to process 2, a solution of the compound VI in water is treated with carboxylic acids of the formulae II–V. These acids can be added in solid form or in solution, e.g. in water-miscible organic solvents such as acetone, ethanol or isopropanol. The reaction and crystallization are carried out as described in process 1.

The compounds of the formula I obtained according to the invention have very good antibacterial activity both against gram-positive and gram-negative microorganisms, as well as against penicillinase- and cephalosporinase-forming microorganisms. Since they moreover have favorable toxicological and pharmacological properties, they are useful chemotherapeutics.

The invention thus also relates to pharmaceuticals for the treatment of microbial infections in mammals, both in humans and in animals, and also in birds and in aquaculture, which contain the physiologically tolerable acid addition salts according to the invention. They can also be used in combination with other active compounds, for example from the penicillin, cephalosporin or amino-glycoside series.

The compounds of the general formula I can be administered subcutaneously, intramuscularly, and in animals also intratracheally or locally, e.g. in the udder of animals giving milk.

Figure 1:
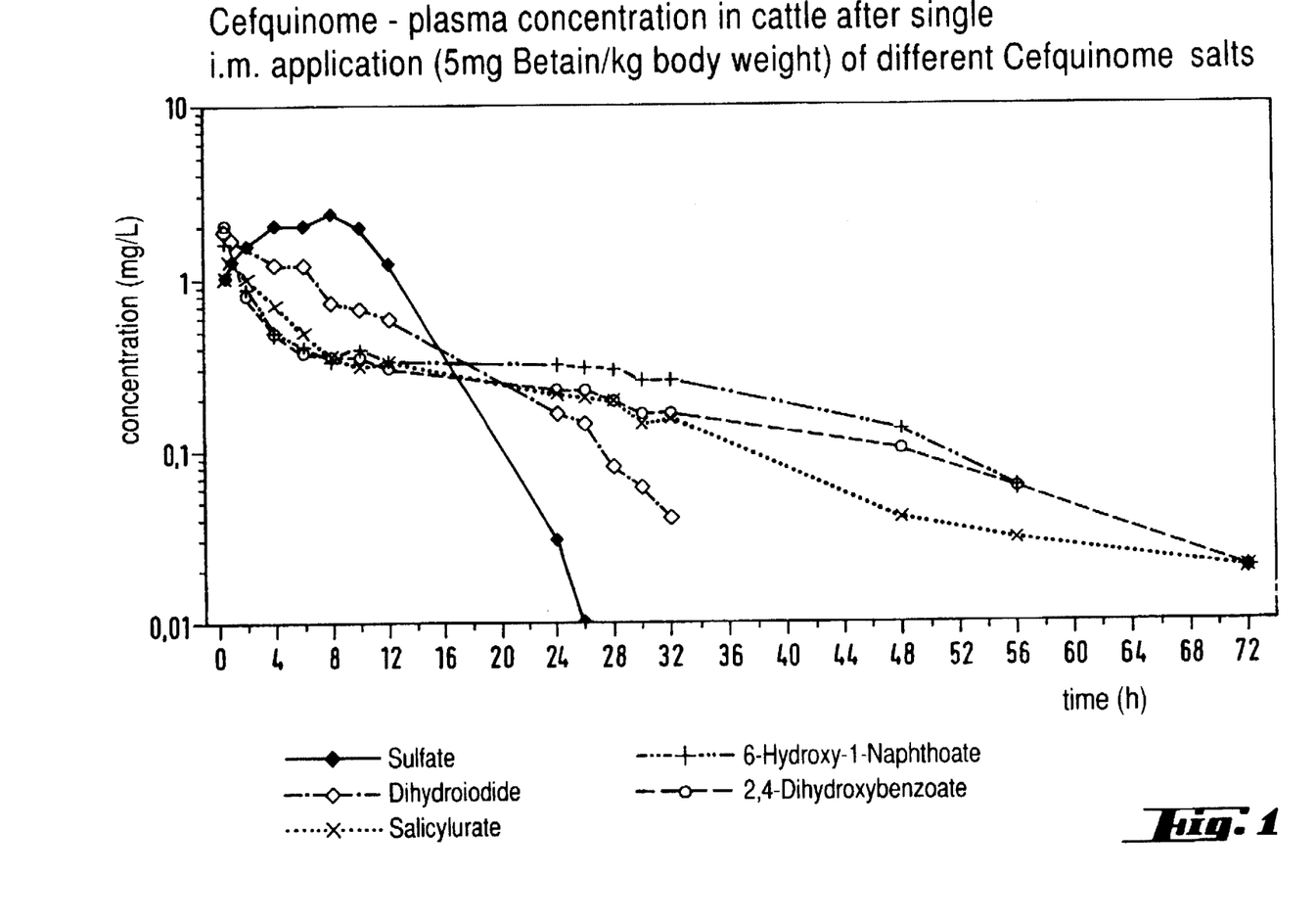

In comparison with the more readily water-soluble salts already known, the acid addition salts according to the invention in this case have remarkable advantages which are based on their low solubility and pharmacokinetics in animals. They are absorbed slowly, e.g. in cattle, after intramuscular (i.m.) administration, and the terminal half-lives (Table 1) and the active compound levels in plasma are distinctly prolonged compared with the known salts. The terminal half-lives ($t_{1/2}$) after single injection (i.m.) of 5 mg of betaine VI (n=2) per kg of body weight for cattle are summarized in Table 1 for compounds according to the invention. The plasma concentration-time curves of cattle after single administration of various cefquinome salts I (n=2) are shown in FIG. 1 (i.m., 5 mg of betaine/kg of body weight). The known salts sulfate and dihydroiodide from DE 3 706 020 are used as a standard. Of the acid addition salts according to the invention, the 6-hydroxy-1-naphthoate (Example 1), the cefquinome-2,4-dihydroxybenzoate (Example 11), and the salicylurate (Example 23) were shown as Examples.

The salts described above which deviate from the ratio 1:1 can also be employed as depot forms and allow the pharmacokinetics in animals to be adjusted.

TABLE 1

Terminal half-lives ($t_{1/2}$) of cefquinome salts according to the invention in cattle after single i.m. administration of 5 mg of betaine/kg of body weight

| Example No. | $t_{1/2}$ h | Example No. | $t_{1/2}$ h | Example No. | $t_{1/2}$ h |
|---|---|---|---|---|---|
| Sulfate | 2.15 | 11 | 16.20 | 18 | 13.00 |
| Dihydroiodide | 4.19 | 12 | 15.20 | 19 | 7.07 |
| 1 | 9.20 | 13 | 9.21 | 20 | 9.39 |
| 2 | 18.8 | 15 | 11.1 | 21 | 9.96 |
| 6 | 5.87 | 16 | 9.16 | 22 | 8.77 |
| 9 | 15.6 | 17 | 17.8 | 23 | 12.70 |

Pharmaceuticals which contain one or more compounds of the formula I as active compound and likewise belong to the subject matter of the present invention can be prepared by mixing the compounds of the formula I with one or more physiologically tolerable excipients, diluents or buffer substances, and bringing them into a preparation form suitable for parenteral or local administration.

Diluents which may be mentioned are, for example, poly-glycols, dimethyl sulfoxide, N-methylpyrrolidone, N,N-dimethylacetamide, ethanol and water. Buffer substances are, for example, organic compounds, e.g. N',N'-dibenzyl-ethylenediamine, diethanolamine, ethylamine, tris-(hydroxymethyl)aminomethane, or inorganic compounds, e.g. phosphate buffer, sodium dicarbonate and sodium carbonate. Suspensions or solutions in water with or without buffer substances are preferably suitable for parenteral administration.

For administration to humans, suitable doses of the compounds of the general formula I are approximately 0.4 to 20 g/day, preferably 0.5 to 4 g/day for an adult of approximately 60 kg body weight.

Individual or, in general, multiple doses can be administered, it being possible for the individual dose to contain the active compound in an amount from approximately 50 to 1000 mg, preferably from approximately 120 to 500 mg.

When administered to animals, in principle all mammals and also birds and fish are suitable, in view of their importance in particular domestic and productive animals. The dosage varies in the individual animal species and can be, for example, between approximately 1.8 and 150, preferably between approximately 5 and 50, mg/kg of body weight of the animal.

The following exemplary embodiments for acid addition compounds of the cephem betaine of the formula VI (n=1: cefpirome, n=2; cefquinome) which can be prepared according to the invention and the contents of the patent claims are used to illustrate the invention further, but do not restrict it thereto.

EXAMPLE 1

Cefquinome-6-hydroxy-1-naphthoate

Process 1

188.0 g (0.3 mol) of cefquinome sulfate are dissolved in 7.4 l of water at room temperature. A solution of 101.6 g (0.54 mol) of 6-hydroxy-1-naphthoic acid in 300 ml of 2N sodium hydroxide solution and 500 ml of water is added dropwise with ice cooling in the course of 30 minutes. During the dropwise addition, a suspension is formed and the temperature falls to 15° C. The mixture is stirred in the ice bath for 45 minutes, and the precipitate is filtered off with suction, suspended in 700 ml of ice water, filtered off with suction again and washed with 300 ml of ice water. The moist precipitate is freeze-dried for 3 days.

Yield: 225 g of title compound+6-hydroxy-1-naphthoic acid.

To remove the excess acid, the mixture is suspended three times in 1.2 l of acetone in each case and stirred for 10 minutes, and the solid is filtered off with suction and washed with 200 ml of acetone each time. After drying in the air, 173.5 g (0.24 mol) of the title compound are obtained as a colorless, finely crystalline product.

Dec.: 190°–210° C.

$^1$H-NMR (270 MHz, DMSO-d$_6$) δ=1.65–2.0 (4H, m); 2.85–3.18 (4H, m); 8 cyclohexene-H; 3.10 and 3.40 (2H, AB, J=18 Hz, SCH$_2$), 3.80 (3H, s, OCH$_3$); 5.03 (1H, d, J=5 Hz, 6-H); 5.33 and 5.42 (2H, AB, J=15 Hz 3'-CH$_2$); 5.63 (1H, dd, J=5.8 Hz, 7-H); 6.72 (1H, s, thiazole-H); 7.21 (4H, m, NH$_2$ and 2 arom. H); 7.43 (1H, dd, J=7 Hz, 1 arom. H); 7.90 (3H, m, 1 Py-H and 2 arom. H); 8.26 (1H, d, J=7 Hz, Py-H); 8.70 (1H, d, J=8 Hz, 1 arom. H); 9.21 (1H, d, J=7 Hz, Py-H); 9.55 (1H, d, J=8 Hz, CONH)

In analogy to Example 1, the cefquinome salts I, n=2, of Table 2 (Examples 2–23, page 11–15) are prepared from cefquinome sulfate and the carboxylic acid X.

In analogy to Example 1, the cefpirome salts 1, n=1, of Table 3 (Examples 24–28, page 16) are prepared from cefpirome sulfate and the carboxylic acid X.

Table 2

| Ex. No. | X | NH$_2$ (bs, 2H) | CONH (1H, d) J = 8 | Thiazole-H (1H, s) | OCH$_3$ (3H, s) | 6-H (1H, d) J = 5 | 7-H (1H, dd) J = 5,8 | 2-CH$_2$ (2H, AB) J = 18 | 3'-CH$_2$ (2H, AB) J = 15 | Pyridine | Cyclohexeno | (X H)$_m$ |
|---|---|---|---|---|---|---|---|---|---|---|---|---|
| 2 | HO-⟨3,4,5-triOH⟩-COOH | 7.21 | 9.55 | 6.71 | 3.80 | 5.05 | 5.66 | 3.25, 3.40 | 5.30, 5.45 | 7.90(1H, dd, J=7) 8.26(1H, d, J=7) 9.20(1H, d, J=7) | 1.70–2.0(4H, m) 2.85–3.15(4H, m) | 6.92(2H, s) |
| 3 | ⟨2-OH-benzoic⟩ COOH | 7.22 | 9.58 | 6.65 | 3.80 | 5.12 | 5.75 | 3.21, 3.40 | 5.38, 5.55 | 7.90(1H, dd, J=7) 8.32(1H, d, J=7) 9.00(1H, d, J=7) | 1.65–2.0(4H, m) 2.9–3.15(4H, m) | 6.75(2H, m) 7.92(1H, dd, J=2,8) 7.70(1H, dd, J=2,8) |
| 4 | HO-⟨4⟩-COOH | 7.22 | 9.55 | 6.72 | 3.80 | 5.05 | 5.65 | 3.25, 3.42 | 5.35, 5.45 | 7.88(1H, dd, J=7) 8.25(1H, d, J=7) 9.20(1H, d, J=7) | 1.65–2.0(4H, m) 2.8–3.2(4H, m) | 6.82, 7.78(4H, AB, J=8) |
| 5 | H$_3$C-⟨2-OH,3-CH$_3$⟩-COOH | 7.22 | 9.55 | 6.72 | 3.80 | 5.08 | 5.73 | 3.20, 3.40 | 5.35, 5.52 | 7.95(1H, dd, J=7) 8.33(1H, d, J=7) 9.02(1H, d, J=7) | 1.65–2.0(4H, m) 2.85–3.18(4H, m) | 2.12(3H, s, CH$_3$) 6.63(1H, dd, J=8) 7.20(1H, dd, J=2,8) 7.58(1H, dd, J=2,8) |

Table 2-continued

| Ex. No. | X | NH₂ (bs, 2H) | CONH (1H, d) J = 8 | Thiazole-H (1H, s) | OCH₃ (3H, s) | 6-H (1H, d) J = 5 | 7-H (1H, dd) J = 5.8 | 2-CH₂ (2H, AB) J = 18 | 3'-CH₂ (2H, AB) J = 15 | Pyridine | Cyclohexeno | (X H)ₘ |
|---|---|---|---|---|---|---|---|---|---|---|---|---|
| 6 | OH, COOH, CH₃ | 7.21 | 9.58 | 6.72 | 3.80 | 5.08 | 5.72 | 3.15, 3.40 | 5.38, 5.50 | 7.90(1H, dd, J=7) 8.28(1H, d, J=7) 9.08(1H, d, J=7) | 1.65-2.0(4H, m) 2.85-3.2(4H, m) | 2.00(3H, s, CH₃) 6.63(1H, d, J=8) 7.08(1H, dd, J=2.8) 7.52(1H, d, J=2.8) |
| 7 | COOH, HO, OCH₃ | 7.20 | 9.55 | 6.72 | 3.80 | 5.05 | 5.66 | 3.20, 3.40 | 5.32, 5.45 | 7.88(1H, dd, J=7) 8.25(1H, d, J=7) 9.12(1H, d, J=7) | 1.7-2.0(4H, m) 2.9-3.2(4H, m) | 3.80(3H, s, OCH₃) 6.86(1H, d, J=8) 7.45(2H, m) |
| 8 | OH, COOH, CH₃O | 7.20 | 9.58 | 6.72 | 3.82 | 5.11 | 5.75 | 3.20, 3.40 | 5.38, 5.63 | 7.90(1H, dd, J=7) 8.31(1H, d, J=7) 8.99(1H, d, J=7) | 1.66-1.95(4H, m) 2.88-3.18(4H, m) | 3.72(3H, s, OCH₃) 6.62(1H, d, J=2.8) 6.93(1H, dd, J=2.8) 7.30(1H, d, J=2.8) |
| 9 | COOH, HO, COOH | 7.22 | 9.56 | 6.71 | 3.80 | 5.03 | 5.66 | 3.10, 3.40 | 5.30, 5.45 | 7.88(1H, dd, J=7) 8.28(1H, d, J=7) 9.20(1H, d, J=7) | 1.6-2.0(4H, m) 2.86-3.24(4H, m) | 7.55(2H, d, J=2) 7.95(1H, d, J=2) |

Table 2-continued (A)

| Ex. No. | X | NH₂ (bs, 2H) | CONH (1H, d) J = 8 | Thiazole-H (1H, s) | OCH₃ (3H, s) | 6-H (1H, d) J = 5 | 7-H (1H, dd) J = 5.8 | 2-CH₂ (2H, AB) J = 18 | 3'-CH₂ (2H, AB) J = 15 | Pyridine | Cyclohexeno | (X H)ₘ |
|---|---|---|---|---|---|---|---|---|---|---|---|---|
| 10 | HO-⌬-COOH (with COOH) | 7.20 | 9.60 | 6.70 | 3.81 | 5.16 | 5.82 | 3.28, 3.40 | 5.40, 5.62 | 7.93(1H, dd, J=7) 8.33(1H, d, J=7) 8.81(1H, d, J=7) | 1.65–2.0(4H, m) 2.9–3.1(4H, m) | 6.70(1H, d, J=8) 7.79(1H, dd, J=2.8) 8.31(1H, d, J=2) |
| 11 | HO-⌬-COOH (with OH) | 7.20 | 9.58 | 6.72 | 3.80 | 5.08 | 5.68 | 3.15, 3.40 | 5.38, 5.50 | 7.85(1H, dd, J=7) 8.28(1H, d, J=7) 9.10(1H, d, J=7) | 1.63–2.05(4H, m) 2.85–3.2(4H, m) | 6.20(1H, d, J=2) 6.25(1H, dd, J=2.8) 7.55(1H, d, J=8) |
| 12 | HO-⌬-COOH (3,5-diOH) | 7.20 | 9.52 | 6.72 | 3.80 | 5.02 | 5.64 | 3.12, 3.40 | 5.35, 5.42 | 7.88(1H, dd, J=7) 8.26(1H, d, J=7) 9.21(1H, d, J=7) | 1.65–2.0(4H, m) 2.88–3.2(4H, m) | 6.40(1H, d, J=2) 6.80(2H, d, J=2) |
| 13 | HO-⌬-COOH (2,5) | 7.21 | 9.58 | 6.72 | 3.81 | 5.09 | 5.70 | 3.18, 3.40 | 5.38, 5.52 | 7.90(1H, dd, J=7) 8.28(1H, d, J=7) 9.05(1H, d, J=7) | 1.65–2.0(4H, m) 2.85–3.2(4H, m) | 6.62(1H, d, J=8) 6.81(1H, dd, J=2.8) 7.15(1H, d, J=2) |

Table 2-continued (A)

| Ex. No. | X | NH₂ (bs, 2H) | CONH (1H, d) J = 8 | Thiazole-H (1H, s) | OCH₃ (3H, s) | 6-H (1H, d) J = 5 | 7-H (1H, dd) J = 5.8 | 2-CH₂ (2H, AB) J = 18 | 3-CH₂ (2H, AB) J = 15 | Pyridine | Cyclohexeno | (X H)ₘ |
|---|---|---|---|---|---|---|---|---|---|---|---|---|
| 14 | (2,6-dihydroxybenzoic acid) | 7.20 | 9.62 | 6.73 | 3.82 | 5.20 | 5.85 | 3.38 (bs) | 5.43 5.66 | 7.92(1H, dd, J=7) 8.35(1H, d, J=7) 8.73(1H, d, J=7) | 1.65-2.0(4H, m) 2.85-3.1(4H, m) | 5.92(1H, d, J=8) 6.05(1H, d, J=8) 6.90(1H, dd, J=8) |
| 15 | (bis-phenol diacid) | 7.20 | 9.60 | 6.72 | 3.82 | 5.11 | 5.75 | 3.22 3.38 | 5.39 5.56 | 7.90(1H, dd, J=7) 8.28(1H, d, J=7) 8.93(1H, d, J=7) | 1.65-2.0(4H, m) 2.85-3.12(4H, m) | 3.8(2H, m, CH₂) 6.78(2H, d, J=8) 7.20(2H, m) 7.60(2H, dd, J=2.8) |
| 16 | (bis-phenol diacid isomer) | 7.20 | 9.52 | 6.72 | 3.80 | 5.05 | 5.66 | 3.38 (bs) | 5.36 5.45 | 7.88(1H, dd, J=7) 8.28(1H, d, J=7) 9.18(1H, d, J=7) | 1.65-2.0(4H, m) 2.85-3.2(4H, m) | 3.8(2H, m, CH₂) 6.75(1H, d, J=8) 6.88(1H, d, J=8) 7.5-7.72(4H, m) |
| 17 | (3-hydroxy-2-naphthoic acid) | 7.20 | 9.58 | 6.70 | 3.80 | 5.10 | 5.75 | 3.22 3.40 | 5.38 5.52 | 7.90(1H, dd, J=7) 8.30(1H, d, J=7) 8.98(1H, d, J=7) | 1.65-2.0(4H, m) 2.83-3.15(4H, m) | 7.01(1H, s); 7.20(1H, d) 7.38(1H, dd, J=8) 7.61(1H, d, J=8); 7.80(1H, d, J=8); 8.32(1H, s) |

Table 2-continued (A) [structure: cephalosporin derivative with aminothiazole, methoxyimino, and pyridinium-(CH₂)ₘ groups]

| Ex. No. | X | NH₂ (bs, 2H) | CONH (1H, d) J = 8 | Thiazole-H (1H, s) | OCH₃ (3H, s) | 6-H (1H, d) J = 5 | 7-H (1H, dd) J = 5,8 | 2-CH₂ (2H, AB) J = 18 | 3'-CH₂ (2H, AB) J = 15 | Pyridine | Cyclohexeno | (X H)ₘ |
|---|---|---|---|---|---|---|---|---|---|---|---|---|
| 18 | [1-COOH, 2-OH naphthyl] | 7.21 | 9.60 | 6.72 | 3.80 | 5.11 | 5.78 | 3.22, 3.38 | 5.40, 5.58 | 7.92(1H, dd, J=7); 8.32(1H, d, J=7); 8.91(1H, d, J=7) | 1.62-2.0(4H, m); 2.82-3.13(4H, m) | 7.00(1H, d, J=8); 7.18(1H, dd, J=8); 7.40(1H, dd, J=8); 7.68(1H, d, J=8); 7.75(1H, d, J=8); 9.20(1H, d, J=8) |
| 19 | [bis-naphthyl-CH₂ linked, COOH, OH substituents] | 7.20 | 9.61 | 6.72 | 3.82 | 5.18 | 5.82 | 3.30, 3.40 | 5.42, 5.62 | 7.92(1H, dd, J=7); 8.35(1H, d, J=7); 8.81(1H, d, J=7) | 1.66-1.98(4H, m); 2.85-3.10(4H, m) | 7.10(1H, dd, J=8); 7.26(2H, dd, J=8); 7.78(2H, d, J=8); 8.18(2H, d, J=8); 8.33(2H, s) |
| 20 | [3-hydroxyphenyl-CH=CH-COOH] | 7.20 | 9.55 | 6.70 | 3.80 | 5.03 | 5.63 | 3.10, 3.40 | 5.32, 5.45 | 7.88(1H, dd, J=7); 8.28(1H, d, J=7); 9.22(1H, d, J=7) | 1.63-2.0(4H, m); 2.85-3.2(4H, m) | 6.40, 7.48(2H, HB, J=15); 6.82(1H, d, J=2); 7.0-7.25(3H, m) |
| 21 | [4-HO-3-OCH₃-phenyl-CH=CH-COOH] | 7.20 | 9.53 | 6.71 | 3.80 | 5.03 | 5.64 | 3.08, 3.38 | 5.33, 5.43 | 7.90(1H, dd, J=7); 8.28(1H, d, J=7); 9.22(1H, d, J=7) | 1.65-2.0(4H, m); 2.88-3.2(4H, m) | 3.80(3H, s) 6.36, 7.48(2H, AB, J=15); 6.80(1H, d, J=8); 7.08(1H, dd, J=2.8); 7.22(1H, dd, J=2.8) |

Table 2-continued

| Ex. No. | X | NH₂ (bs, 2H) | CONH (1H, d) J=8 | Thiazole-H (1H, s) | OCH₃ (3H, s) | 6-H (1H, d) J=5 | 7-H (1H, dd) J=5.8 | 2-CH₂ (2H, AB) J=18 | 3'-CH₂ (2H, AB) J=15 | Pyridine | Cyclohexeno | (X H)ₘ |
|---|---|---|---|---|---|---|---|---|---|---|---|---|
| 22 | HO-⬡-CH₂COOH | 7.22 | 9.53 | 6.70 | 3.82 | 5.02 | 5.66 | 3.08 3.40 | 5.32 5.42 | 7.88(1H, dd, J=7) 8.28(1H, d, J=7) 9.21(1H, d, J=7) | 1.65–2.0(4H, m) 2.85–3.2(4H, m) | 3.40(2H, s, CH₂) 6.68, 7.05(4H, AB, J=8) 12.25 bs, COOH |
| 23 | ⬡(CONHCH₂COOH)(OH) | 7.21 | 9.53 9.05 | 6.72 | 3.80 | 5.05 | 5.64 | 3.10 3.40 | 5.30 5.42 | 7.88(1H, dd, J=7) 8.28(1H, d, J=7) 9.25(1H, d, J=7) | 1.70–2.0(4H, m) 2.88–3.2(4H, m) | 3.98(2H, d, CH₂) 6.92(2H, m) 7.40(1H, dd, J=2.8) 7.86(1H, d, J=8) |

TABLE 3

Formula I, n = 1

| Ex. No. | X | NH₂ (bs, 2H) | CONH (1H, d) J=8 | Thiazole-H (1H, s) | OCH₃ (3H, s) | 6-H (1H, d) J=5 | 7-H (1H, dd) J=5,8 | 2-CH₂ (2H, AB) J=18 | 3'-CH₂ (2H, AB) J=15 | Pyridine | Cyclohexeno | (X H)ₘ |
|---|---|---|---|---|---|---|---|---|---|---|---|---|
| 24 | COOH, HO–, –OH | 7.21 | 9.54 | 6.71 | 3.80 | 5.05 | 5.68 | 3.08 3.40 | 5.28 5.48 | 7.90(1H, dd, J=7) 8.38(1H, d, J=7) 9.15(1H, d, J=7) | 2.1–2.3(2H, m) 3.05–3.17(2H, m) 3.2–3.35(2H, m) | 6.20(1H, d, J=2) 6.25(1H, dd, J=2,8) 7.56(1H, d, J=8) |
| 25 | COOH, HO–, –COOH | 7.20 | 9.58 | 6.72 | 3.80 | 5.08 | 5.72 | 3.20 3.40 | 5.25 5.48 | 7.92(1H, dd, J=7) 8.38(1H, d, J=7) 9.03(1H, d, J=7) | 2.1–2.3(2H, m) 3.02–3.2(2H, m) 3.25–3.35(2H, m) | 6.62(1H, d, J=8) 7.82(1H, dd, J=2,8) 8.30(1H, d, J=2) |
| 26 | COOH, HO–, HO–, –OH | 7.20 | 9.55 | 6.72 | 3.80 | 5.02 | 5.65 | 3.30 3.42 | 5.22 5.45 | 7.88(1H, dd, J=7) 8.36(1H, d, J=7) 9.22(1H, d, J=7) | 2.1–2.3(2H, m) 3.0–3.2(2H, m) 3.25–3.5(2H, m) | 6.92(2H, s) |
| 27 | COOH, naphthyl-OH | 7.20 | 9.55 | 6.72 | 3.80 | 5.05 | 5.63 | 3.35 3.42 | 5.22 5.47 | 7.88(1H, dd, J=7) 8.33(1H, d, J=7) 9.23(1H, d, J=7) | 2.1–2.3(2H, m) 3.03–3.22(2H, m) 3.3–3.45(2H, m) | 7.20(2H, m), 7.42(1H, dd, J=7), 7.90(2H, m), 8.70 (1H, d, J=8) |
| 28 | CH=CHCO, HO–, OCH₃ | 7.20 | 9.52 | 6.70 | 3.80 | 5.02 | 5.62 | 3.10 3.40 | 5.20 5.45 | 7.90(1H, dd, J=7) 8.37(1H, d, J=7) 9.26(1H, d, J=7) | 2.1–2.3(2H, m) 3.0–3.2(2H, m) 3.2–3.45(2H, m) | 3.80(3H, s) 6.38; 7.48(2H, HB, J=15) 6.80(1H, d, J=8) 7.08(1H, dd, J=2,8) 7.22(1H, dd, J=2,8) |

EXAMPLE 29

Cefquinome-2, 4-dihydroxybenzoate

Process 2

5 ml of 2N sodium hydroxide solution are added at room temperature to a solution of 3.14 g (5 mmol) of cefquinome sulfate in 125 ml of water. The betaine solution formed is cooled to 15° C. A solution of 1.39 g (9 mmol) of 2,4-dihydroxybenzoic acid in 10 ml of acetone is then added dropwise in the course of 5 minutes. The suspension obtained is stirred in an ice bath for 5 hours, and the precipitate is filtered off with suction, washed with 5 ml of ice water and dried over phosphorus pentoxide in vacuo. The crude product (1.98 g) is stirred with 40 ml of acetone for 2 hours, and the precipitate is filtered off with suction, washed with 10 ml of acetone and dried over $P_2O_5$ in vacuo.

Yield: 1.873 g (2.74 mmol) of colorless crystalline product

Dec.: 175°–185° C.

The compound is identical in all properties with the compound from Example 11.

EXAMPLE 30

Cefquinome-2,3-dihydroxy-5-methylbenzoate

In analogy to Example 29, 1.81 g (2.6 mmol) of the title compound are obtained as a pale brown crystalline product from 3.14 g (5 mmol) of cefquinome sulfate and 1.51 g (9 mmol) of 2,3-dihydroxy-5-methylbenzoic acid.

$^1$H-NMR (270 MHz, DMSO-$d_6$): δ=1.63–1.98 (4H, m); 2.12 (3H,s,CH$_3$); 2.86–3.18 (4H, m); 3.10 and 3.40 (2H, AB, J=18 Hz, SCH$_2$); 3.81 (3H, s, OCH$_3$); 5.10 (1H, d, J=5 Hz, 6-H); 5.34 and 5.55 (2H, AB, J=15 Hz, 3'-CH$_2$); 5.75 (1H, dd, J=5.8 Hz, 7-H); 6.69 (1H, d, J=2 Hz, arom. H); 6.72 (1H, s, thiazole-H); 7.00 (1H, d, J=2 Hz, arom. H); 7.20 (2H, bs, NH$_2$); 7.90 (1H, dd, J=7 Hz, Py-H); 8.30 (1H, d, J=7 Hz, Py-H); 9.00 (1H, d, J=7 Hz, Py-H); 9.58 (1H, d, J=8 Hz, CONH).

We claim:
1. A compound of the formula I in which
n is equal to 1 or 2 and
m is 0.4–2.6, and where
X is the anion of a phenolic carboxylic acid of the formulae II a–d or the anion of a hydroxyphenylacetic acid of the formula III or the anion of a hydroxycinnamic acid of the formula IV or the anion of a hydroxyhippuric acid of the formula V where R and R' independently of one another are hydrogen, carboxyl, hydroxyl, halogen, a straight-chain or branched saturated or unsaturated aliphatic $C_1$–$C_5$-alkyl radical or $C_1$–$C_5$-alkoxy radical and where X can also be X/2 in the case of a diprotic acid.

2. A compound of the formula I as claimed in claim 1, wherein X is the anion of a carboxylic acid of the formulae II–V, in which R and R' independently of one another are hydrogen, carboxyl, hydroxyl, methyl or methoxy and where m is 0.5–2.

3. A compound of the formula I as claimed in claim 1 or 2, wherein X is the anion of a compound selected from the following group of acids:

dihydroxybenzoic acids, such as 2,4-, 2,5- or 3,5-dihydroxybenzoic acid, trihydroxybenzoic acids, such as gallic acid, hydroxydicarboxylic acids, such as 4-hydroxyiso-phthalic acid, hydroxynaphthalenecarboxylic acids, such as 2-hydroxy-naphthalene-1-carboxylic acid or 6-hydroxynaphthalene-1-carboxylic acid, methylenebishydroxybenzoic acids, such as 5,5'-methylenebis-4-hydroxybenzoic acid, methylenebishydroxynaphthoic acids, such as embonic acid, hydroxycinnamic acids such as ferulic acid, hydroxyhippuric acids such as salicyluric acid.

4. A method of treating a bacterial infection in a patient in need thereof which comprises administering to the patient an antibacterially effective amount of a compound of formula I

[Structure (I)]

in which
n is equal to 1 or 2 and
m is 0.4–2.6, and where
X is the anion of a phenolic carboxylic acid of the formulae II a–d

[Structures IIa, IIb, IIc, IId]

or the anion of a hydroxyphenylacetic acid of the formula III

[Structure III: R, HO-phenyl-CH$_2$COOH]

or the anion of a hydroxycinnamic acid of the formula IV

[Structure IV: R, HO-phenyl-CH=CH-COOH]

or the anion of a hydroxyhippuric acid of the formula V

[Structure V: R, HO-phenyl-CONHCH$_2$COOH]

where R and R' independently of one another are hydrogen, carboxyl, hydroxyl, halogen, a straight-chain or branched saturated or unsaturated aliphatic $C_1$–$C_5$-alkyl radical or $C_1$–$C_5$-alkoxy radical and where X can also be X/2 in the case of a diprotic acid.

5. A method of claim 4 wherein X is the anion of a carboxylic acid of the formula II–V, in which R and R' independently of one another are hydrogen, carboxyl, hydroxyl, methyl or methoxy and where m is 0.5–2.

6. A method of claim 4 wherein X is the anion of a compound selected from the following lists of acids:

2,4-dihydroxybenzoic acid;
2,5-dihydroxybenzoic acid;
3,5-dihydroxybenzoic acid;
gallic acid;
4-hydroxyisophthalic acid;
2-hydroxynaphthalene-1-carboxylic acid;
6-hydroxynaphthalene-1-carboxylic acid;
5,5'-methylenebis-4-hydroxybenzoic acid;
embonic acid;
ferulic acid; and
salicyluric acid.

7. A pharmaceutical composition comprising a compound of formula I

(I)

in which
n is equal to 1 or 2 and
m is 0.4–2.6, and where
X is the anion of a phenolic carboxylic acid of the formulae
II a–d

IIa

IIb

IIc

IId or the anion of a hydroxyphenylacetic acid of the formula III

III or the anion of a hydroxycinnamic acid of the formula IV

IV or the anion of a hydroxyhippuric acid of the formula V

V where R and R' independently of one another are hydrogen, carboxyl, hydroxyl, halogen, a straight-chain or branched saturated or unsaturated aliphatic $C_1$–$C_5$-alkyl radical or $C_1$–$C_5$-alkoxy radical and where X can also be X/2 in the case of a diprotic acid, together with physiologically tolerable excipients, diluents and buffers.

8. A pharmaceutical composition of claim 7 wherein X is the anion of a carboxylic acid of the formula II–V, in which R and R' independently of one another are hydrogen, carboxyl, hydroxyl, methyl or methoxy and where m is 0.5–2.

9. A pharmaceutical composition of claim 7 wherein X is the anion of a compound selected from the following lists of acids:

2,4-dihydroxybenzoic acid;
2,5-dihydroxybenzoic acid;
3,5-dihydroxybenzoic acid;
gallic acid;
4-hydroxyisophthalic acid;
2-hydroxynaphthalene-1-carboxylic acid;
6-hydroxynaphthalene-1-carboxylic acid;
5,5'-methylenebis-4-hydroxybenzoic acid;
embonic acid;
ferulic acid; and
salicyluric acid.

* * * * *